United States Patent [19]

Johnson

[11] Patent Number: 4,851,008
[45] Date of Patent: Jul. 25, 1989

[54] BONE IMPLANT PROSTHESIS WITH SUBSTANTIALLY STRESS-FREE OUTER SURFACE

[75] Inventor: Wesley Johnson, Minnetonka, Minn.

[73] Assignee: Orthomet, Inc., Minneapolis, Minn.

[21] Appl. No.: 151,108

[22] Filed: Feb. 1, 1988

[51] Int. Cl.$^4$ ............................ A61F 2/28; A61F 2/32
[52] U.S. Cl. ......................................... 623/16; 623/18; 623/22; 128/92 YZ; 128/92 YK
[58] Field of Search ................................... 623/18–23, 623/16; 128/92 R, 92 Y, 92 YZ, 92 YY, 92 YK, 92 YW, 92 YT

[56] References Cited

U.S. PATENT DOCUMENTS

| | | |
|---|---|---|
| 3,605,123 | 9/1971 | Hahn . |
| 3,855,638 | 12/1974 | Pilliar . |
| 4,199,824 | 4/1980 | Niederer .......................... 623/18 X |
| 4,231,120 | 11/1980 | Day ................................... 623/20 X |
| 4,355,427 | 10/1982 | Schneider ............................ 623/19 |
| 4,375,703 | 3/1983 | Evans et al. ......................... 623/21 |
| 4,406,023 | 9/1983 | Harris . |
| 4,479,271 | 10/1984 | Bolesky et al. . |
| 4,516,277 | 5/1985 | Butel .................................... 623/23 |
| 4,589,883 | 5/1986 | Kenna . |
| 4,628,920 | 12/1986 | Mathys, Jr. et al. ........... 128/92 YZ |

FOREIGN PATENT DOCUMENTS 2932744  2/1980  Fed. Rep. of Germany ........ 623/22

OTHER PUBLICATIONS

Fundamentals of Machine Component Design, Robert Juvinall, 1983, pp. 222–225.

Primary Examiner—Richard J. Apley
Assistant Examiner—David J. Bender
Attorney, Agent, or Firm—James R. Haller; Gregory P. Kaihoi; Mary P. Bauman

[57] ABSTRACT

A bone implant prosthesis having an outer stress-free surface and a subsurface carried generally beneath and parallel to the outer surface for bearing tensile stresses. The prosthesis of the invention includes a plurality of slots undercutting the outer surface of the prosthesis thus forming a stress bearing subsurface to free the outer surface from being subjected to substantial stresses. The stress-free outer surface is readily adaptable to receive a porous coating to enhance bone ingrowth without decreasing the stress resistance characteristics of the prosthesis.

7 Claims, 4 Drawing Sheets

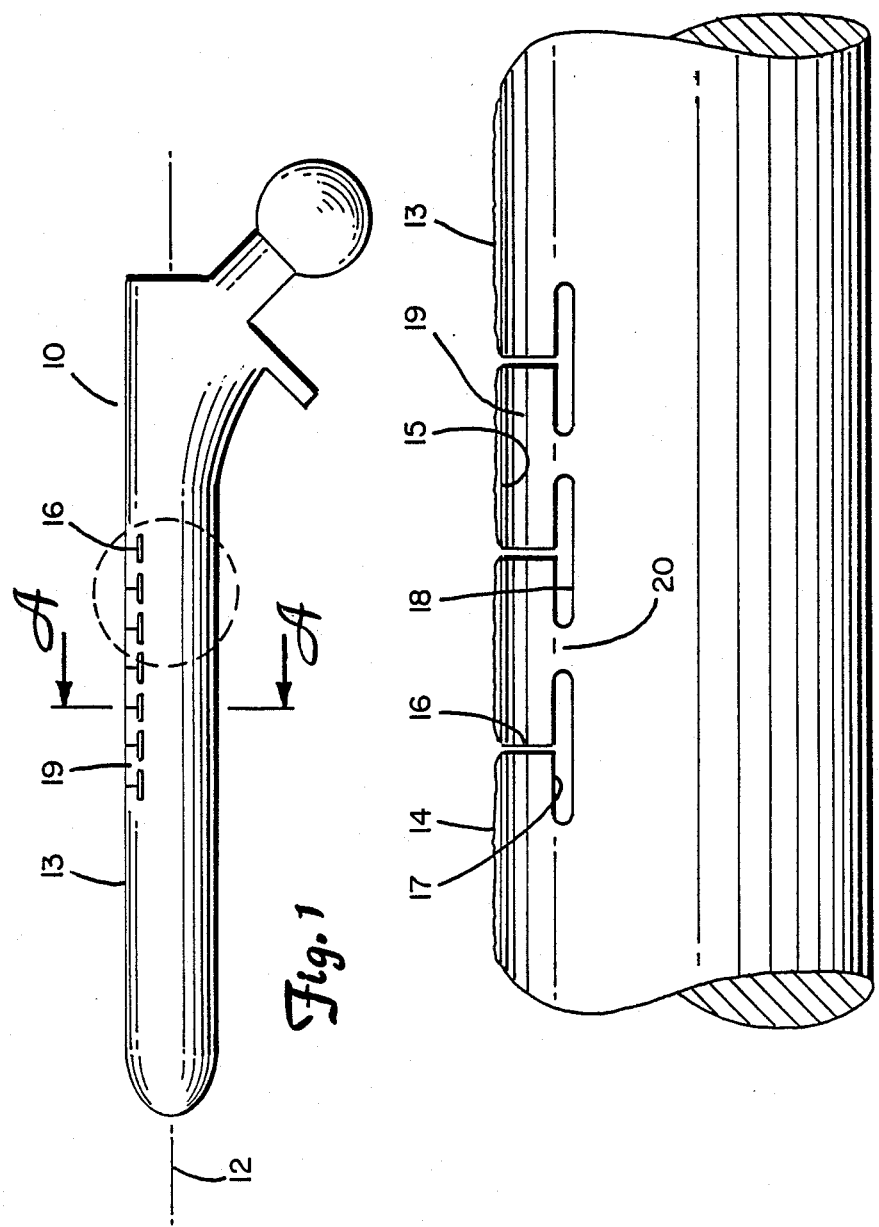

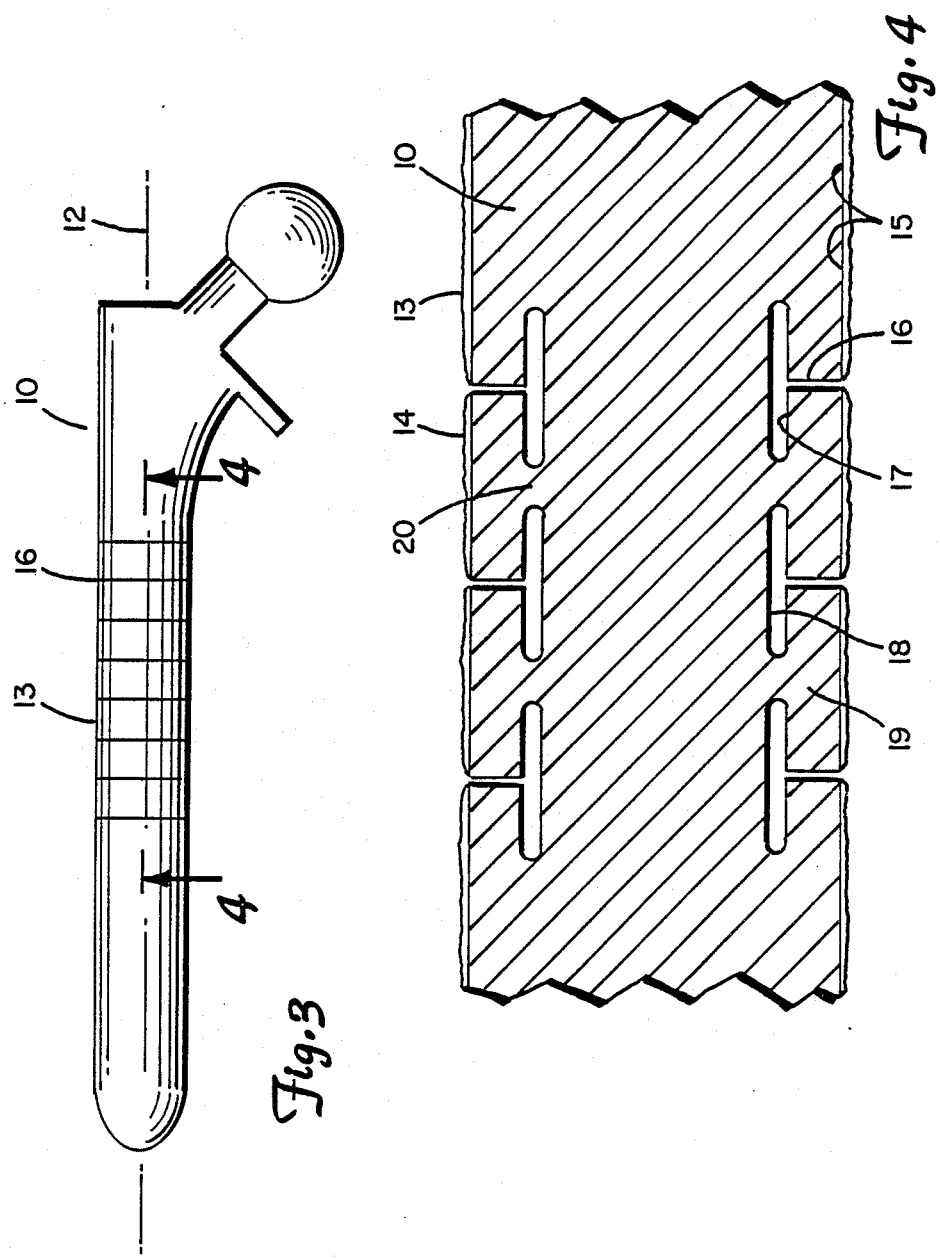

BONE IMPLANT PROSTHESIS WITH SUBSTANTIALLY STRESS-FREE OUTER SURFACE

FIELD OF THE INVENTION

The invention relates to bone implant prostheses and, more particularly, to bone implant prostheses which are capable of withstanding the application of large stresses.

BACKGROUND OF THE INVENTION

It has been common in the past, in the case of serious bone fractures in which simple resetting is contraindicated, to replace all or part of the bone with a suitable implant generally made of titanium or another metal. An example of an implant of this type is a femoral implant which includes a stem for insertion in the intermedullary canal of the femur, a neck portion at an angle to the stem, and a capitulum carried at the end of the neck. Because of the shape of the prosthesis and the high stress location in which it is employed, its outer or lateral surface is subjected to substantial bending stresses, putting the outer surface in tension, during each step that a patient takes. Since titanium can withstand repeated cycles (i.e. $10^8$ cycles) of stress of about 80,000 psi, smooth titanium implants are generally used for this type of application.

It is often preferable to render porous the outer surfaces of the prosthesis by applying a thin coating of metallic beads to enhance the ingrowth of bone material. The porous metallic bead coatings are generally sintered onto the surface of the prosthesis utilizing relatively high temperatures. The combination of the high temperature and the application of the beads causes some of the beads to penetrate the surface of the prosthesis forming notches or stress-concentration sites. These stress concentration sites are likely locations from which cracks may form in the outer surface of the prosthesis as it is continuously cycled in tension. Cracks are very undesirable because they can significantly weaken the prosthesis and can cause the prosthesis to fail.

The characteristics of the surface of the prosthesis affects the amount of stress that the prosthesis can withstand at a given number of stressing cycles. The amount of stress that a prosthesis can withstand, while staying within its elastic limit, at a large number of cycles of stress (e.g., $10^8$ cycles) is referred to as the fatigue endurance limit. Titanium and titanium alloys are particularly notch-sensitive in that when prostheses formed of these materials are notched in stressed areas, the fatigue endurance limit may be significantly reduced.

It is preferrable to have bone implant prostheses having porous coatings because bone ingrowth into the coatings can significantly strengthen the bone-prosthesis bond. However, it has been found that prostheses of the type described above are prone to premature failure due to the abundant stress concentration sites and their tendency to promote cracking. In general, prostheses with porous outer surfaces can withstand repeated (e.g., $10^8$) tensile stress cycles of only about 20,000 psi.

The metallic bead coatings are further preferred because they have elastic qualities that are somewhat similar to those of the metal upon which they are placed. This feature enables both the metal implant and the thin coating to stretch and flex together without interrupting the bond between them.

Ceramic porous coatings are also used, but since ceramic materials do not possess good elastic characteristics, slight bending of the femoral implant (such as that caused by normal walking) may crack and loosen the ceramic beaded surface.

It is desired to have a bone implant prosthesis with a porous outer surface possessing the strength to withstand the repeated stresses of normal implanted use.

SUMMARY OF THE INVENTION

The invention relates to a bone implant prosthesis for the surgical reconstruction and repair of bone fractures and other abnormalities in bone structure. The prosthesis comprises a body portion having a stress-free outer surface and a stress-bearing subsurface generally parallel to and spaced beneath the outer surface. A series of generally parallel spaced slots extend into the prosthesis, the slots having widened lower portions which form the stress-bearing subsurface. A discontinuous plane surface is formed by the floor of the slots which, when the prosthesis is stressed, becomes the plane bearing the maximum tensile stress. In this configuration, the outer surface of the prosthesis is rendered essentially tensile stress-free and therefore may be provided with a porous coating without weakening the stress bearing characteristics of the prosthesis.

BRIEF DESCRIPTION OF THE DRAWINGS

FIG. 1 is an elevation view of the bone implant prosthesis of the invention;

FIG. 2 is a detailed view of the portion of FIG. 1 within the dashed circle;

FIG. 3 is an elevation view of an alternative embodiment of the invention showing slots extending around the circumference of the prosthesis;

FIG. 4 is a cross-sectional view of the prosthesis of FIG. 3 taken along line 4—4 thereof;

DETAILED DESCRIPTION OF THE PREFERRED EMBODIMENTS

Figure 1A:
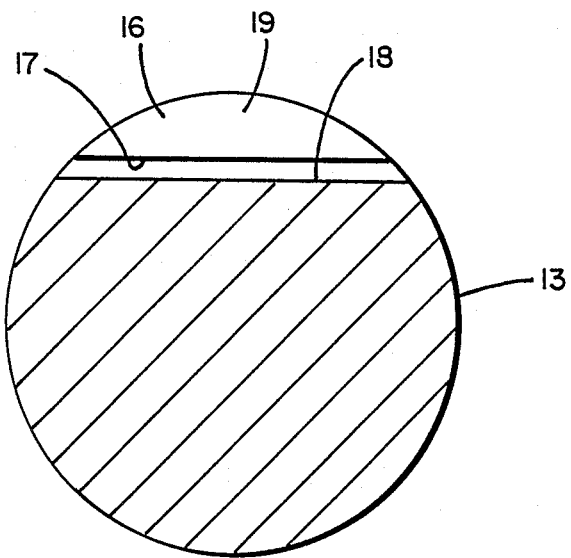
FIG. 1A is a cross-sectional view of the prosthesis of FIG. 1 taken along line A—A thereof.

The bone implant prosthesis of the invention is of the type intended to be surgically implanted into living tissue for reconstruction of body structure. The device of the invention is particularly suited for but not limited to use as a femoral implant due to its favorable stress bearing characteristics, as that type of implant prosthesis is generally subjected to large cyclic stresses.

The invention comprises a bone implant prosthesis (10) having an essentially tensile stress-free outer surface (13) upon which may be applied a porous coating (14), and a stress-bearing subsurface (18). As shown in FIGS. 1 and 2, the stress-free outer surface (13) is created by undercutting the outer surface (13) with a series of slots (16). The slots (16) are preferably "T" shaped and spaced such that a minimal metal ligament (20) is present between adjacent slots (16). The result is an outer surface (13) comprised of a plurality of relatively large sections of material (19) suspended generally above a lower subsurface (18) by thin ligaments (20). In this configuration, tensile stresses applied to the prosthesis (10) are borne by the subsurface (18) and are not transferred to the outer surface (13).

Preferably, the slots (16) are designed so that, under extreme loading conditions, the portion of the slot (16) extending to the outer surface (13) of the prosthesis (10) is adequately sized to prevent adjacent outer surface portions (19) from contacting one another. If the outer surface portions (19) were allowed to contact one another, the outer surface (13) would be stressed while the portions (19) were in contact. This contact is undesirable because stressing of the outer porous surface (13) may cause cracks to develop. Therefore, it is desirable to utilize slots (16) of adequate width to prevent the external surface portions (19) from contacting one another even under extreme loading conditions.

The slots (16) are preferably formed by passing a generally "T" shaped electrode through the surface of the prosthesis (10) to a depth of approximately one tenth of an inch. The electrode is supplied with an electrical current having a high voltage which substantially melts a path through the prosthesis (10). The electrode may be moved in a straight line path through several lateral surfaces of the prosthesis (10) thus forming straight slots (16) through the prosthesis (10) as shown in FIGS. 1, 1A and 2.

The slots (16) are preferably T-shaped in cross-section and, in one embodiment, are straight, formed as chords across the curved surface of the prosthesis (10). The cross bars of the T's are generally spaced beneath the outer surface (13) of the body and have a widened portion (17) defining a stress-bearing sub-surface (18). Perfect alignment or parallelism of slots (16) is not required, nor must the slots (16) be uniformly spaced from one another.

Alternatively, the electrode may be inserted into the prosthesis (10) in a radial direction with the longitudinal portion directed perpendicular to the axis (12) of the prosthesis (10) and rotated approximately 90 degrees when it reaches a desired depth beneath the surface (13). The prosthesis (10) may then be rotated through at least 360 degrees to cut a slot (16) substantially entirely around the perimeter of the prosthesis (10) spaced from the outer surface (13). The electrode could then be rotated 90 degrees and removed in a radial direction from the prosthesis (10). A plurality of identical slots (16) may be made, spaced from one another by a predetermined distance, creating an essentially tensile stress-free sub-surface (18) about the perimeter of the prosthesis (10). This procedure would create a smooth subsurface (18) comprised of a plurality of slots (16) that could be subjected to substantial stresses thus allowing the external periphery of the prosthesis (10) to carry a porous coating (14). A prosthesis of the type described above is shown in FIGS. 3 and 4.

Figure 5:
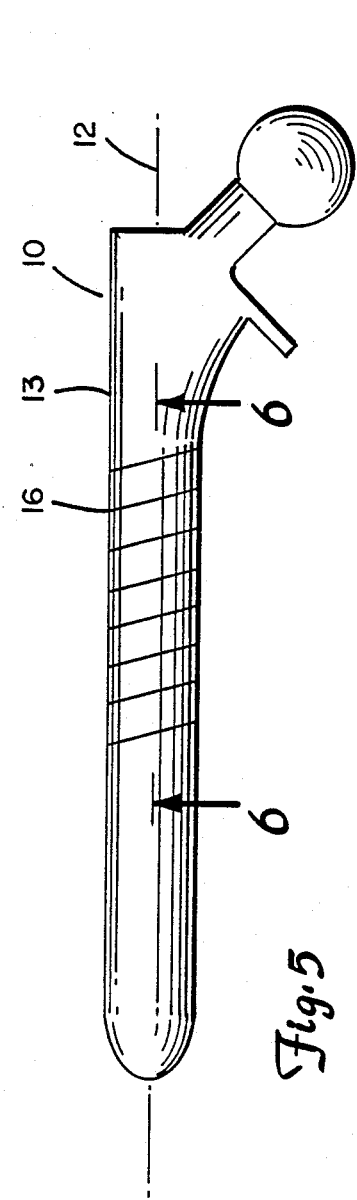
FIG. 5 is an elevation view of an alternative embodiment of the invention showing spirally arranged slots about the circumference of the prosthesis.
Figure 6:
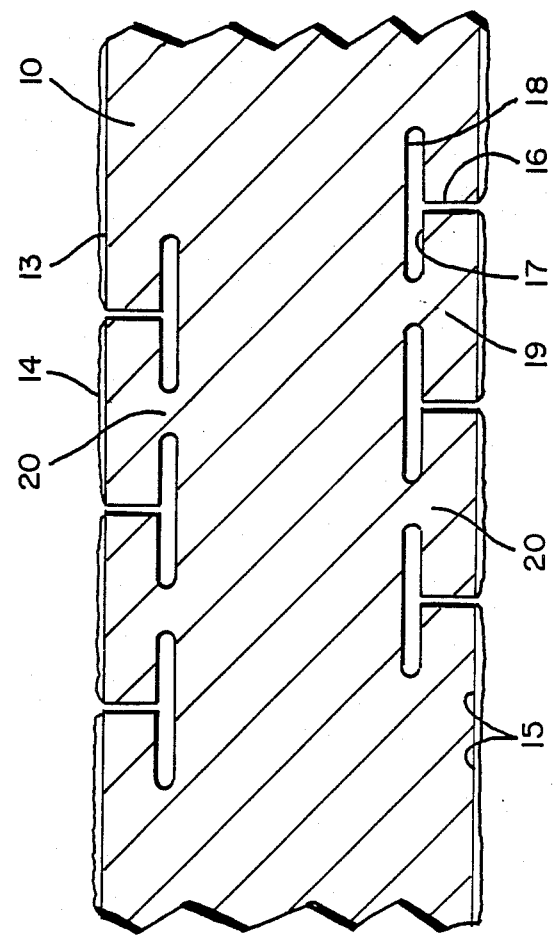
FIG. 6 is a cross sectional view of the prosthesis of FIG. 5 taken along line 6—6 thereof.

In another embodiment of the invention, shown in FIGS. 5 and 6, the slot (16) may be embodied as a single helical channel extending around the perimeter of the prosthesis (10), spaced from the outer surface (13), along a portion of the length of the prosthesis (10).

There are many useful applications for these concepts. One of the applications involves the addition of a porous coating (14) (e.g., plasma spray or sintered bead) to the stress-free outer surface (13) that is created. Some of the porous coatings create small stress concentration sites (15) in the titanium surface of the prosthesis. Applying the coating to an essentially tensile stress-free surface neutralizes the notch sensitivity of the titanium, thereby dramatically increasing the endurance limit for repeated stressings of the implant.

The essentially tensile stress-free surface is readily acceptable for application of a hydroxylapatite (HA) coating. HA coatings are becoming very popular within the orthopedic community. One of the major problems in utilizing such coatings in the past has been the propensity for the coating to separate from the substrate. This separation may be due, in part, to tensile stresses within the substrate which create a strain gradient between the coating and the substrate.

The creation of an essentially tensile stress-free surface on the implant may favorably enhance osteointegration (bone ingrowth or bone ongrowth). One of the major problems in total joint replacement is the presence of a fibrocartilaginous layer between the implant and the bone. In some cases, this layer is the result of a dramatic strain gradient between implant and supporting bone structure. Such a strain gradient creates micromotion at the interface. This micromotion promotes fibrous tissue formation. In the case of severe micromotion, fibrous tissue formation may be progressive, leading to implant loosening and failure.

In various embodiments of the invention, the depth of the slots (16), or stress neutralizing channels, may be varied to alter the structural stiffness of the implant. The structural stiffness could then be optimized along the length of the stem to create a more uniform (i.e., physiological) stress pattern within the supporting bone structure.

Some of the potential implant uses for this invention include hip stem, acetabular cup, total knee (tibial tray and femoral component), spinal fixation rods and plates, trauma plates and intramedullary rod implants.

While a preferred embodiment of the present invention has been described, it should be understood that various changes, adaptations and modifications may be made therein without departing from the spirit of the invention and the scope of the appended claims.

What is claimed is:

1. A bone implant prosthesis comprising a body portion having an outer surface containing stress concentration sites, and a series of elongated generally parallel slots formed through the outer surface, the slots having widened floor portions defining a stress-bearing discontinuous smooth subsurface spaced beneath the outer surface, the slots rendering the outer surface of the prosthesis essentially free of tensile stresses when in use.

2. The bone implant prosthesis of claim 1 wherein the outer stress-free surface carries a porous coating to enhance bone ingrowth.

3. The bone implant prosthesis of claim 1 wherein the sub-surface is substantially smooth and free of stress concentration sites.

4. The prosthesis of claim 1 in which the slots are sized to prevent adjacent outer surface portions thereof from contacting one another when the prosthesis is in use.

5. A bone implant prosthesis comprising a body portion adapted to encounter bone and having an outer surface containing stress concentration sites, the body portion having formed therein a series of elongated generally "T"-shaped slots, the cross bar portions of adjacent T-shaped slots cooperating to define a stress-bearing, discontinuous smooth subsurface generally parallel to and spaced beneath the outer surface of the prosthesis, said slots rendering the outer surface of the prosthesis essentially free of tensile stresses when in use.

6. A bone implant prosthesis comprising a body portion formed as an integral unit and having a porous outer surface to promote bone growth therein, the body portion being provided with a series of elongated generally parallel spaced slots extending through the outer surface, the slots having widened portions spaced beneath the outer surface together defining a smooth discontinuous stress-bearing subsurface, the slots rendering the porous outer surface essentially free of tensile stresses developed during use of the prosthesis.

7. The prosthesis of claim 6 in which the slots are generally "T" shaped with the cross bar of the T forming the floor of each slot.

* * * * *